(12) United States Patent
Kandel et al.

(10) Patent No.: US 7,354,578 B2
(45) Date of Patent: *Apr. 8, 2008

(54) METHOD OF TUMOR REGRESSION WITH VEGF INHIBITORS

(75) Inventors: Jessica Kandel, New York, NY (US); Jocelyn Holash, Alameda, CA (US); Darrell Yamashiro, Westwood, NJ (US); Jianzhong Huang, New York, NY (US); George Yancopoulos, Yorktown Heights, NY (US); John Rudge, Mahopac, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 503 days.

This patent is subject to a terminal disclaimer.

(21) Appl. No.: 10/860,958

(22) Filed: Jun. 4, 2004

(65) Prior Publication Data

US 2004/0265309 A1  Dec. 30, 2004

Related U.S. Application Data

(60) Provisional application No. 60/476,425, filed on Jun. 6, 2003.

(51) Int. Cl.
*A61K 38/18* (2006.01)
*C07K 14/71* (2006.01)
*C12N 15/62* (2006.01)

(52) U.S. Cl. .............. 424/134.1; 424/192.1; 514/2; 514/12; 530/350; 536/23.4

(58) Field of Classification Search .............. None
See application file for complete search history.

(56) References Cited

U.S. PATENT DOCUMENTS

| 6,897,294 | B2 * | 5/2005 | Davis-Smyth et al. ...... 530/350 |
| 2005/0032699 | A1 * | 2/2005 | Holash et al. ................ 514/12 |
| 2005/0112061 | A1 * | 5/2005 | Holash et al. ............. 424/1.49 |
| 2005/0196340 | A1 * | 9/2005 | Holash et al. ............. 424/1.69 |

FOREIGN PATENT DOCUMENTS

WO   WO00/75319 A   12/2000

OTHER PUBLICATIONS

Gerber et al. (2000) Cancer Res. 60:6253-6258.
Kim et al. (2002) Proc. Natl. Acad. Sci. USA 99:11399-404.
Holash et al. (2002) Proc. Natl. Acad. Sci. USA 99:11393-8.
Internet Articles, VEGF Trap in Treating Patients With Solid Tumors or Non-Hodgkin's Lymphoma 'Online! XP002305401 Retrieved from the Internet: URL:http://www.clinicaltrials.gov/ct/show/NCT00045266?order=4>.

* cited by examiner

*Primary Examiner*—Christine J Saoud
*Assistant Examiner*—Jon M Lockard
(74) *Attorney, Agent, or Firm*—Valeta Gregg, Esq.

(57) ABSTRACT

Methods of regressing or inhibiting a tumor in a subject by administering an agent capable of blocking, inhibiting, or ameliorating vascular endothelial growth factor (VEGF)-mediated activity to a subject in need thereof such that the tumor is regressed or inhibited. The method of the invention results in a reduction of tumor size and inhibition of tumor metastases. This method is particularly useful for patients suffering from bulky, metastatic cancers.

6 Claims, 3 Drawing Sheets

METHOD OF TUMOR REGRESSION WITH VEGF INHIBITORS

CROSS-REFERENCE TO RELATED APPLICATIONS

This application claims the benefit under 35 USC § 119(e) of U.S. Provisional 60/476,425 filed 6 Jun. 2003, which application is herein specifically incorporated by reference in its entirety.

FIELD OF THE INVENTION

The invention relates to methods of promoting regression of tumors and metastases by inhibiting vascular endothelial growth factor (VEGF) activity.

DESCRIPTION OF RELATED ART

Vascular endothelial growth factor (VEGF)expression is nearly ubiquitous in human cancer, consistent with its role as a key mediator of tumor neoangiogenesis. Blockade of VEGF function, by binding to the molecule or its VEGFR-2 receptor, inhibits growth of implanted tumor cells in multiple different xenograft models (see, for example, Gerber et al. (2000) Cancer Res. 60:6253-6258). A soluble VEGF antagonist, termed a "VEGF Trap" has been described (Kim et al. (2002) Proc. Natl. Acad. Sci. USA 99:11399-404; Holash et al. (2002) Proc. Natl. Acad. Sci. USA 99:11393-8), which applications are specifically incorporated by reference in their entirety.

BRIEF SUMMARY OF THE INVENTION

In a first aspect, the invention features a method of regressing or reducing the size of a tumor in a subject in need thereof, comprising administering a therapeutically effective amount of an agent capable of blocking, inhibiting, or ameliorating VEGF-mediated activity to the subject, wherein the tumor is regressed. The term "regression" means to decrease or reduce the size of a tumor, e.g., to shrink the tumor.

The agent capable of blocking, inhibiting, or ameliorating VEGF-mediated activity in specific embodiments is a VEGF antagonist. More specifically, the VEGF antagonist includes a VEGF trap selected from the group consisting of acetylated Flt-1(1-3)-Fc, Flt-1(1-3$_{R->N}$)-Fc, Flt-1(1-3$_{\Delta B}$)-Fc, Flt-1(2-3$_{\Delta B}$)-Fc, Flt-1(2-3)-Fc, Flt-1D2-VEGFR3D3-FcΔC1(a), Flt-1D2-Flk-1D3-FcΔC 1(a), and VEGFR1R2-FcΔC1(a). In a specific and preferred embodiment, the VEGF trap is VEGFR1R2-FcΔC1(a) (also termed VEGF trap$_{R1R2}$) having the nucleotide sequence set forth in SEQ ID NO: 1 and the amino acid sequence set forth in SEQ ID NO: 2. The invention encompasses the use of a VEGF trap that is at least 90%, 95%, 98%, or at least 99% homologous with the nucleotide sequence set forth in SEQ ID NO: 1 and/or the amino acid sequence set forth in SEQ ID NO:2. In other specific embodiments, the agent is an antibody, lipid, nucleic acid, small molecule, aptamer, antisense molecule, carbohydrate, peptidomimetic, or hapten.

The subject to be treated by the method of the invention is preferably a human subject having one or more tumors, e.g., a human patient suffering from cancer with bulky disease, including orthotopic tumors, spontaneously metastatic legions, and spontaneously arising tumors; however, the method of the invention is useful for any mammal in need of treatment, including domestic species. In further embodiments, the method of the invention may be used in combination with other therapeutic methods, including other agents used in the treatment of cancer.

Administration of the agent may be by any method known in the art, including subcutaneous, intramuscular, intradermal, intraperitoneal, intravenous, intranasal, or oral routes of administration.

In a second aspect, the invention features a method of regressing metastases, e.g., such as lung metastases, in a subject in need thereof, comprising administering to the subject an agent capable of blocking, inhibiting, or ameliorating VEGF-mediated activity.

In a third aspect, the invention features a method of treating a tumor such that a tumor is reduced in size, comprising administering an agent capable of blocking, inhibiting, or ameliorating VEGF-mediated activity to a subject in need thereof wherein the tumor is reduced in size.

In a fourth aspect, the invention features a method of treating a metastatic cancer in a subject suffering thereof, comprising administering an agent capable of blocking, inhibiting, or ameliorating VEGF-mediated activity to a subject in need thereof, wherein the tumor is reduced in size.

Other objects and advantages will become apparent from a review of the ensuing detailed description.

DETAILED DESCRIPTION

Figure 1:
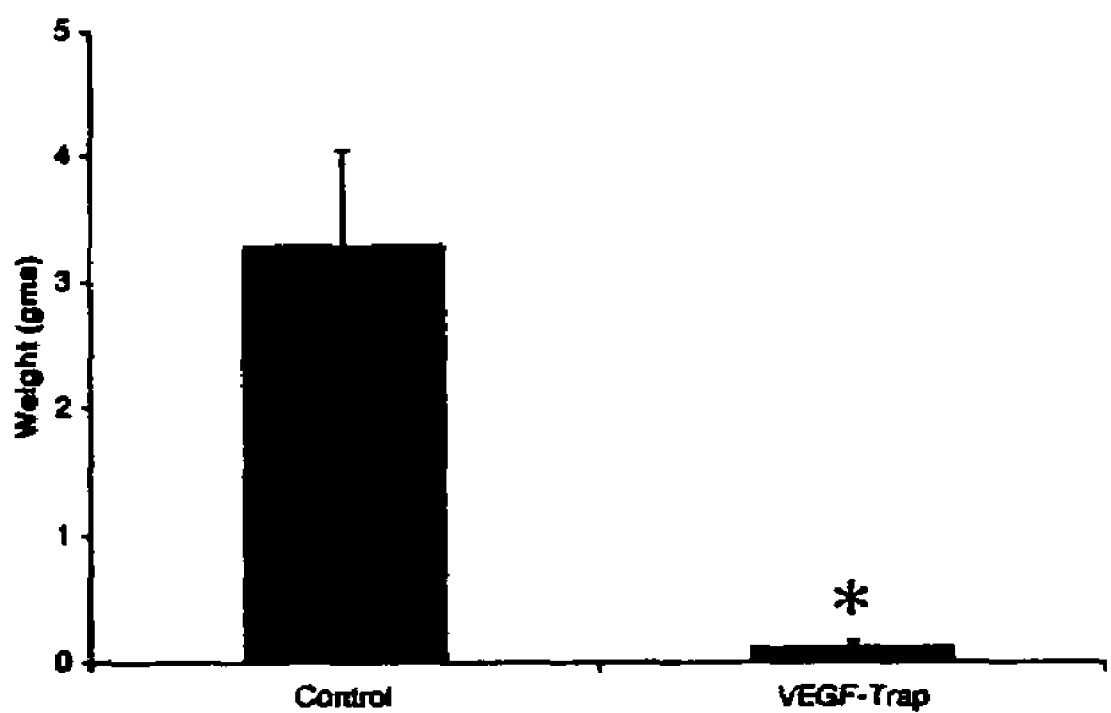
FIG. 1. Involution of xenograph vessels and tumor regression. Mice were treatment with VEGF trap (500 mg) or an equal amount of human Fc protein. Mice were euthanized at days 1, 5, 8, 15, and 27 after initiation of injections (mean tumor weights±SEM: 5.5±1.02 g, 4.2±0.66 g, 3.9±0.87 g, 3.5±0.91 g, 2.7+0.8 g, respectively). Only treated mice survived until day 36 (mean tumor weight±SEM: 1.2 g±0.3 g, P<0.0002 vs. day 0 controls). Error bars represent standard error of the mean.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

General Description

Previous studies have focused on the role of VEGF in models of minimal residual disease, in which inhibitors are used with the goal of preventing tumor growth rather than treating large lesions with established vasculature and distant metastases. In support of this approach has been the observation that established vascular networks in normal tissues, in which recruited smooth muscle-like perivascular cells adhere to endothelium, do not appear to become destabilized when VEGF is withdrawn or antagonized (Benjamin et al. (1999) J. Clin. Invest. 103:159-165). Tumors engineered to stop VEGF production after growth and development of a vascular network exhibit regression primarily of those vessels which lack vascular mural cells (Benjamin et al. (1999) supra).

The invention disclosed herein results from experiments to determine if the apparent susceptibility of endothelial-only tumor vessels to VEGF withdrawal might be relative, rather than absolute, and that this pathological vasculature may remain globally dependent on VEGF. Withdrawal of tumor-derived VEGF might still allow for survival of vessels whose endothelium requires only the low levels of VEGF provided by associated stromal cells. Such tumor vessels, when compared to the vasculature of normal tissues, might still be relatively immature and pathological, and thus vulnerable to VEGF blockade. Thus, it was hypothesized that blockade of both tumor and stromal VEGF might potentially disrupt endothelial-perivascular cell signaling in at least some tumors, leading to destabilization of vasculature and frank tumor regression.

The experiments described below were conducted with a recently described soluble decoy receptor the VEGF trap described in Holash et al. (2002) Proc. Natl. Acad. Scie. USA 99:11393-11398. This construct incorporates domains of both VEGFR-1 and VEGFR-2, and binds VEGF with significantly higher affinity than previously reported VEGF antagonists. In order to investigate whether blocking the additional VEGF in the tumor vessel microenvironment would produce disruption of pre-existing vasculature, the VEGF trap VEGFR1R2-FcΔC1 was administered to animals with established xenografts and metastases.

Definitions

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

By the term "blocker", "inhibitor", or "antagonist" is meant a substance that retards or prevents a chemical or physiological reaction or response. Common blockers or inhibitors include but are not limited to antisense molecules, antibodies, antagonists and their derivatives. More specifically, an example of a VEGF blocker or inhibitor is a VEGF receptor-based antagonist including, for example, an anti-VEGF antibody, or a VEGF trap such as VEGFR1R2-FcΔC1(a) (SEQ ID NOs:1-2). For a complete description of VEGF-receptor based antagonists including VEGFR1R2-FcΔC1(a), see PCT publication WO/00/75319, the contents of which is herein incorporated by reference in its entirety.

A "small molecule" is defined herein to have a molecular weight below about 500 Daltons, and may include chemical as well as peptide molecules.

Nucleic Acid Constructs

Individual components of the VEGF-specific fusion proteins of the invention may be constructed by molecular biological methods known to the art with the instructions provided by the instant specification. These components are selected from a first cellular receptor protein, such as, for example, VEGFR1; a second cellular receptor protein, such as, for example, VEGFR2; a multimerizing component, such as an Fc.

Specific embodiments of the VEGF-specific fusion proteins useful in the methods of the invention comprise a multimerizing component which allows the fusion proteins to associate, e.g., as multimers, preferably dimers. Preferably, the multimerizing component comprises an immunoglobulin derived domain. Suitable multimerizing components are sequences encoding an immunoglobulin heavy chain hinge region (Takahashi et al. 1982 Cell 29:671-679); immunoglobulin gene sequences, and portions thereof.

The nucleic acid constructs encoding the fusion proteins useful in the methods of the invention are inserted into an expression vector by methods known to the art, wherein the nucleic acid molecule is operatively linked to an expression control sequence. Host-vector systems for the production of proteins comprising an expression vector introduced into a host cell suitable for expression of the protein are known in the art. The suitable host cell may be a bacterial cell such as *E. coli*, a yeast cell, such as *Pichia pastoris*, an insect cell, such as *Spodoptera frugiperda*, or a mammalian cell, such as a COS, CHO, 293, BHK or NS0 cell.

Antisense Nucleic Acids

In one aspect of the invention, VEGF-mediated activity is blocked or inhibited by the use of VEGF antisense nucleic acids. The present invention provides the therapeutic or prophylactic use of nucleic acids comprising at least six nucleotides that are antisense to a gene or cDNA encoding VEGF or a portion thereof. As used herein, a VEGF "antisense" nucleic acid refers to a nucleic acid capable of hybridizing by virtue of some sequence complementarity to a portion of an RNA (preferably mRNA) encoding VEGF. The antisense nucleic acid may be complementary to a coding and/or noncoding region of an mRNA encoding VEGF. Such antisense nucleic acids have utility as compounds that prevent VEGF expression, and can be used for tumor regression. The antisense nucleic acids of the invention are double-stranded or single-stranded oligonucleotides, RNA or DNA or a modification or derivative thereof, and can be directly administered to a cell or produced intracellularly by transcription of exogenous, introduced sequences.

The VEGF antisense nucleic acids are of at least six nucleotides and are preferably oligonucleotides ranging from 6 to about 50 oligonucleotides. In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof and can be single-stranded or double-stranded. In addition, the antisense molecules may be polymers that are nucleic acid mimics, such as PNA, morpholino oligos, and LNA. Other types of antisense molecules include short double-stranded RNAs, known as siRNAs, and short hairpin RNAs, and long dsRNA (>50 bp but usually ≧500 bp).

Inhibitory Ribozymes

In aspect of the invention, a tumor may be regressed in a subject suffering from cancer by decreasing the level of VEGF activity by using ribozyme molecules designed to catalytically cleave gene mRNA transcripts encoding VEGF, preventing translation of target gene mRNA and, therefore, expression of the gene product.

Ribozymes are enzymatic RNA molecules capable of catalyzing the specific cleavage of RNA. The mechanism of ribozyme action involves sequence-specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246. While ribozymes that cleave mRNA at site-specific recognition sequences can be used to destroy mRNAs encoding VEGF, the use of hammerhead ribozymes is preferred. Hammerhead ribozymes cleave mRNAs at locations dictated by flanking regions that form complementary base pairs with the target mRNA. The sole requirement is that the target mRNA has the following sequence of two bases: 5'-UG-3'. The construction and production of hammerhead ribozymes is well known in the art. The ribozymes of the present invention also include RNA endoribonucleases (hereinafter "Cech-type ribozymes") such as the one that occurs naturally in *Tetrahymena thermophila* (known as the IVS, or L-19 IVS RNA). The Cech-type ribozymes have an eight base pair active site that hybridizes to a target RNA sequence where after cleavage of the target RNA takes place. The invention encompasses those Cech-type ribozymes that target eight base-pair active site sequences that are present in the gene encoding VEGF.

Generation of Antibodies to VEGF Proteins

In another aspect of the invention, the invention may be practiced with an anti-VEGF antibody or antibody fragment capable of binding and blocking VEGF activity. Anti-VEGF antibodies are disclosed, for example, in U.S. Pat. No. 6,121,230, herein specifically incorporated by reference. The term "antibody" as used herein refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant regions, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Within each IgG class, there are different isotypes (eg. $IgG_1$, $IgG_2$, $IgG_3$, $IgG_4$). Typically, the antigen-binding region of an antibody will be the most critical in determining specificity and affinity of binding.

Antibodies exist as intact immunoglobulins, or as a number of well-characterized fragments produced by digestion with various peptidases. For example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the terms antibody, as used herein, also includes antibody fragments either produced by the modification of whole antibodies, or those synthesized de novo using recombinant DNA methodologies (e.g., single chain Fv)(scFv) or those identified using phase display libraries (see, for example, McCafferty et al. (1990) Nature 348:552-554).

Methods for preparing antibodies are known to the art. See, for example, Kohler & Milstein (1975) Nature 256: 495-497; Harlow & Lane (1988) *Antibodies: a Laboratory Manual,* Cold Spring Harbor Lab., Cold Spring Harbor, N.Y.). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity. Techniques for the production of single chain antibodies or recombinant antibodies (U.S. Pat. Nos. 4,946,778; 4,816,567) can be adapted to produce antibodies used in the fusion proteins and methods of the instant invention. Also, transgenic mice, or other organisms such as other mammals, may be used to express human or humanized antibodies. Alternatively, phage display technology can be used to identify antibodies and heteromeric Fab fragments that specifically bind to selected antigens.

Antibody Screening and Selection

Screening and selection of preferred antibodies can be conducted by a variety of methods known to the art. Initial screening for the presence of monoclonal antibodies specific to a target antigen may be conducted through the use of ELISA-based methods, for example. A secondary screen is preferably conducted to identify and select a desired monoclonal antibody for use in construction of the multi-specific fusion proteins of the invention. Secondary screening may be conducted with any suitable method known to the art. One preferred method, termed "Biosensor Modification-Assisted Profiling" ("BiaMAP") is described in co-pending U.S. Ser. No. 60/423,017 filed 01 Nov. 2002, herein specifically incorporated by reference in its entirety. BiaMAP allows rapid identification of hybridoma clones producing monoclonal antibodies with desired characteristics. More specifically, monoclonal antibodies are sorted into distinct epitope-related groups based on evaluation of antibody: antigen interactions.

Treatment Population

Human patients suffering from cancer with bulky disease, including orthotopic tumors, spontaenously metastatic lesions, and/or spontaneously arising tumors are candidates for treatment by the methods of the invention. A variety of anti-angiogenic agents prevent growth of implanted xenografts, a setting which mimics the status of minimal residual disease in human cancer patients. However, many patients with resistant cancers have bulky primary lesions or metastases. This population are at a high risk of dying from their disease, and would benefit greatly from anti-angionenic drugs capable of regressing pre-exising tumors and metastases.

Methods of Administration

The invention provides methods of treatment comprising administering to a subject an effective amount of an agent of the invention. In a preferred aspect, the agent is substantially purified (e.g., substantially free from substances that limit its effect or produce undesired side-effects). The subject is preferably an animal, e.g., such as cows, pigs, horses, chickens, cats, dogs, etc., and is preferably a mammal, and most preferably human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents.

In another embodiment, the active agent can be delivered in a vesicle, in particular a liposome (see Langer (1990) Science 249:1527-1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

Cellular Transfection and Gene Therapy

The present invention encompasses the use of nucleic acids encoding the VEGF-specific fusion proteins of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell. Reintroduction of transfected cells may be accomplished by any method known to the art, including re-implantation of encapsulated cells. The compositions are administered (e.g., by injection into a muscle) to a subject in an amount sufficient to elicit a therapeutic response. An amount adequate to accomplish this is defined as "a therapeutically effective dose or amount."

In another aspect, the invention provides a method of regressing a tumor in a human comprising transfecting a cell with a nucleic acid encoding a VEGF-specific fusion protein of the invention, wherein the nucleic acid comprises an inducible promoter operably linked to the nucleic acid encoding the VEGF-specific fusion protein. For gene therapy procedures in the treatment or prevention of human disease, see for example, Van Brunt (1998) Biotechnology 6:1149-1154.

Combination Therapies

In numerous embodiments, the VEGF-specific fusion proteins of the present invention may be administered in combination with one or more additional compounds or therapies. Combination therapy includes administration of a single pharmaceutical dosage formulation which contains a VEGF-specific fusion protein and one or more additional agents; as well as administration of a VEGF-specific fusion protein and one or more additional agent(s) in its own separate pharmaceutical dosage formulation. For example, a VEGF-specific fusion protein of the invention and a hypoglycemic agent can be administered to the patient together in a single oral dosage composition such as a tablet or capsule, or each agent administered in separate oral dosage formulations. Where separate dosage formulations are used, the VEGF-specific fusion protein of the invention and one or more additional agents can be administered concurrently, or at separately staggered times, i.e., sequentially.

Pharmaceutical Compositions

Pharmaceutical compositions useful in the practice of the method of the invention include a therapeutically effective amount of an active agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous, subcutaneous, or intramuscular administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent of the invention that will be effective in the treatment methods of the invention can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 50-5000 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

Kits

The invention also provides an article of manufacturing comprising packaging material and a pharmaceutical agent contained within the packaging material, wherein the pharmaceutical agent comprises at least one VEGF-specific fusion protein of the invention and wherein the packaging material comprises a label or package insert which indicates that the VEGF-specific fusion protein can be used for tumor regression.

Specific Embodiments

Previous investigators have reported that those tumor vessels in which a layer of vascular mural cells lies adjacent to endothelium are protected from the effects of tumor-derived VEGF withdrawal (see, for example, Abramovitch et al. (1999) Cancer Res. 59:5012-5016). We reasoned that the effect of VEGF produced locally by endothelial or stromal cells should not be altered by cessation of tumor VEGF production. In addition, a low level of VEGF might not be captured by agents with less affinity for this factor than the soluble receptor VEGF trap construct studied (Kim et al. (2002) Proc. Natl. Acad. Sci. USA 99:11399-11404; Holash et al. (2002) Proc. Natl. Acad. Sci. USA 99:11393-11398, which applications are herein specifically incorporated by reference in their entirety). If the role of VEGF in endothelial-vascular mural cell trafficking is critical to tumor vessel integrity, even mature tumor vasculature might be susceptible to disruption by such a high-affinity anti-VEGF agent. The results provided herein show that the VEGF inhibitor used caused concurrent apoptosis of both endothelial and recruited perivascular cells in pre-existing tumors, without the apparent protective effect of the vascular mural cell layer.

As shown in the experiments described below, the VEGF trap almost completely abolished tumor vasculature in experimental animals with established tumors, causing rapid progressive disappearance of both endothelial and vascular mural components. Vessel involution was followed by significant regression of large pre-existing xenografts. In addition, pre-existing lung micrometastases markedly decreased in both size and cell number, displaying apoptosis after one dose of the VEGF trap, suggesting a role for VEGF-dependent homeostasis in these lesions as well. Since the pattern of lung microvessels adjacent to micrometastases did not appear to be altered by exposure to VEGF trap, regression may be linked to disruption of other VEGF functions (such as permeability); such micrometastases may be supplied by diffusion prior to reaching a size where tumor cell hypoxia stimulates neoangiogenesis. The results provided provide evidence for the importance of VEGF as a target in cancer therapy, and provide evidence that anti-VEGF strategies may not only halt tumor growth but produce actual regression. These results support the use of a VEGF inhibitor in the treatment of patients with metastatic, bulky cancers, as well as those with minimal residual disease.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Regression of Established Tumors During VEGF-Trap Injection

Xenograft Model.

SK-NEP-1 Wilms tumor cells (American Type Culture Collection, Manassas, Va.), SY5Y neuroblastoma cells (American Type Culture Collection, Manassas, Va.) or HUH hepatoblastoma cells (HuH-6, RIKEN BioResource Center, Ibaraki, Japan) were maintained in culture with McCoy's 5A medium (Mediatech, Fisher Scientific, Springfield, N.J.), supplemented with 15% fetal bovine serum and 1% penicillin-streptomycin (Gibco, Grand Island, N.Y.). Cells were grown at 37° C. in 5% CO2 until confluent, harvested, counted with trypan blue staining, and washed and resuspended in sterile phosphate-buffered saline (PBS) at a concentration of 107 cells per milliliter. Xenografts were established in 4-6 week old female NCR nude mice (NCI-Frederick Cancer Research and Development Center, Frederick, Md.) by intrarenal injection of 106 cells from one of the following human cell lines: SK-NEP-1, SY5Y or hepatoblastoma cells and allowed to grow for the specified periods of time.

For experiments utilizing each cell line, after 5-6 weeks large tumors were palpable in all mice, and a cohort was randomly selected (n=10) to provide day 0 controls. Remaining mice were divided into two groups, and injected twice weekly with VEGF trap (500 mg; Regeneron Pharmaceuticals, Tarrytown, N.Y.) or an equal amount of human Fc protein in the same volume of vehicle. For the experiment with Wilms tumor, mice (n=5, control and treated animals, at each time point) were euthanized at day 1, 5, 8, 15, and 27 after initiation of injections, and tumors excised and weighed. Only treated mice survived until day 36 (n=10). Similarly, for the studies using the hepatoblastoma and neuroblastoma cell lines, mice were monitored for tumor regression and growth with calipers, and euthanized at intervals.

Results.

Wilms Tumor: Orthotopically implanted SK-NEP-1 human Wilms tumor cells grown for 5 weeks formed large retroperitoneal tumors (mean weight, 5.8 g+1.1 g). Injections of VEGF trap (500 mg) or Fc control protein were then given intraperitoneally biweekly. Subsets of treated and control mice were euthanized at intervals. By day 36, mean tumor weight had decreased by 79.3% (day 36, 1.2 g±0.3 g, p<0.0002) (FIG. 1). On gross examination, the VEGF trap-treated tumors were markedly pale as compared to control tumors with strikingly diminished vasculature by day 15, and virtual absence of vessels by day 36. The kidney, which was grossly replaced by tumor tissue, reemerged as the tumor tissue receded, returning to a remarkably normal appearance by day 36.

Figure 2:
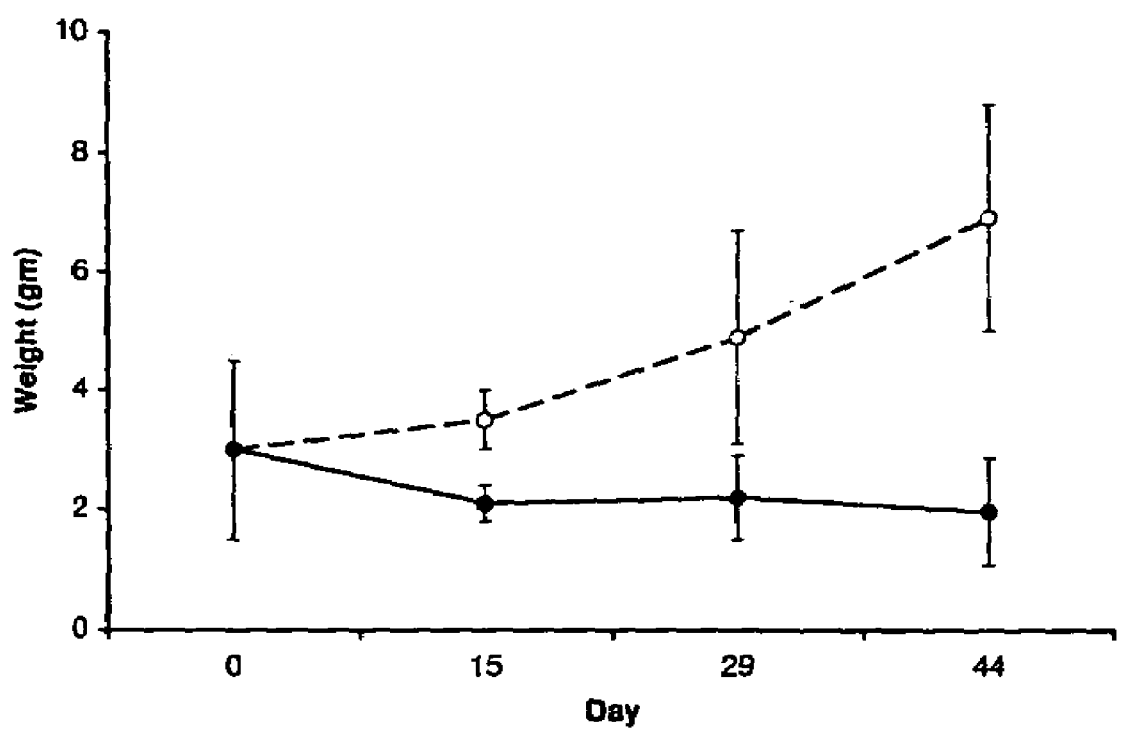
FIG. 2. Progressive decrease in luminal perfusion, and in endothelial and vascular mural compartments of vasculature with VEGF trap treatment.

Hepatoblastoma: Intrarenally implanted HUH-6 human hepatoblastoma cells grown for 5 weeks formed large retroperitoneal tumors (mean weight of 3.0±0.5 g). Injections of VEGF trap (500 mg) or Fc control protein were then given intraperitoneally biweekly. Subsets of treated and control mice were euthanized at intervals. After initiation of VEGF-Trap, tumor growth completely halted, reaching an apparent plateau by day 15 which was sustained to the end of the experiment at day 44 (mean tumor weights 2.1±0.19 g, day 15; 2.2+0.4 g, day 29; 2.0+0.3 g, day 44, p=0.058 vs. day 0 controls) (FIG. 2). In contrast, control tumors continued to grow, and were significantly larger at day 44 than VEGF Trap-treated tumors at the same time point (6.9+1.0 g vs. 2.0+0.3g, respectively; P=0.0112).

Neuroblastoma: Similar to the other cell lines, SY5Y neuroblastoma cells formed large retroperitoneal tumors. 5 weeks after tumor implantation, tumors in untreated mice reached a size of 6.65±0.84 g, and within a week (D6) had reached a size of 7.28±1.16 g (n=10), at which time all mice in the control cohort had to be sacrificed. At this time, mice treated with VEGF Trap had tumors of 3.31±0.96 g (n=5, p<0.0278), suggesting that regression had occurred.

Example 2

Involution of Existing Vasculature in Wilms Tumor During VEGF Trap Injection

Lectin perfusion. Prior to euthanasia, selected mice at each time point underwent intravascular injection of fluorescein-labeled *Lycopersicon esculentum* lectin (100 µg in 100 µl of saline, Vector Laboratories, Burlingame, Calif.) into the left ventricle. The vasculature was fixed by infusion of 1% paraformaldehyde (pH 7.4) in PBS, and then washed by perfusion of PBS, as described in Thurston et al. (1996) Am. J. Physiol. 271:H2547-2562.

Digital Image Analysis.

Digital images from the fluorescein-labeled lectin studies were acquired from a Nikon E600 fluorescence microscope (10× objective) with a Spot RT Slider digital camera (Diagnostic Instruments, Sterling Heights, Mich.) and stored as TIFF files. Quantitative assessment of angiogenesis and tumor vessel architecture was performed by computer-assisted digital image analysis as described by Wild et al. (2000) Microvasc. Res. 59:368-376, except that fluorescein-labeled lectin (FL) was substituted for phycoerythrin (PE)-conjugated monoclonal antibody to CD-31. The fraction of FL-positive pixels per total field was quantified by a computer-assisted method as described (Wild et al. (2000) supra). Changes in vessel architecture were evaluated by quantifying branch points (nodes), end points, and total vessel length. Images were analyzed after application of a common threshold value, inversion of the image, morphological erosion, and skeletonization, using a combination of Adobe Photoshop (Adobe Inc., Mountain View, Calif.) and Image Processing Tool Kit (Reindeer Graphics, Inc., Raleigh, N.C.) as described (Wild et al. (2000) supra).

PECAM-1 Immunostaining.

Control and VEGF-Trap-treated tumors were immunostained with a rat anti-mouse platelet-endothelial cell adhesion molecule-1 (PECAM-1) monoclonal antibody (Research Diagnostics, Inc., Flanders, N.J.), and a rabbit anti-rat biotinylated secondary antibody (Zymed Laboratories, Inc., South San Francisco, Calif.). Enhanced horseradish peroxidaseconjugated streptavidin, and a substrate chromogen, AEC (3-amino-9-ethyl carbazole) were used to visualize the signal (HistoStain-Plus kit, Zymed), and slides examined using a Nikon Eclipse E600 microscope.

aSMA Immunostaining.

Monoclonal anti-a-smooth muscle actin (aSMA) antibody (Sigma Chemical Co., St. Louis, Mo.) was incubated at room temperature for 30 min. Specimens were then incubated with a 1:400 rabbit anti-mouse biotinylated secondary antibody. Fluorescein labeled avidin was used to develop a green fluorescent signal. Specimens were analyzed and photographed by fluorescence microscopy.

Confocal Microscopy.

Serial optical sections of lectin-perfused tumor were acquired using a confocal laser scanning microscope (Zeiss LSM 410). A computerized algorithm was used to assign color codes to fluorescein-labeled vessels by depth of field.

Results.

Vascular alterations caused by VEGF trap treatment was examined as follows: To outline the vessel lumens, fluorescein-labeled *Lycopersicon esculentum* lectin was injected intravascularly in tumor-bearing animals. One day after the first injection of VEGF trap (day 1), a marked decrease in lectin outlined vessels was observed. In a separate experiment, quantitative image analysis was used to compare microvessel density (MVD), total length of lectin-perfused vessels, vessel ends, and branch points/nodes in tumors 1 day after VEGF trap injection. Tumor weights were unchanged as compared to controls at the same time point. VEGF trap-treated tumor vasculature showed significant decreases in all parameters measured as compared to untreated controls: MVD by 54% (37,599±23,428 vs. 81,167±39,363, mean white pixel count±standard deviation (SD), p=0.037), total vessel length by 42% (3,340±1,244 vs. 5,725±+1,438, p=0.01), vessel ends by 63% (127±22 vs. 347±178, p<0.004), and branches points/nodes by 80% (17±6 vs. 85±40, p<0.004). Vasculature progressively disappeared, resulting in almost complete absence of vessels by day 15. No changes in vessel architecture were observed in normal tissues in VEGF trap-treated animals (data not shown).

These perfusion studies were compared with the status of endothelial and recruited perivascular cells in tumors by performing specific immunostaining for these populations in the same samples. The results demonstrated a similarly timed decrease in endothelial cells: PECAM-1-immunopositive vasculature diminished after one injection of VEGF trap (day 1), with abolition of endothelium by day 15. Necrosis of tumor cells was evident by day 5.

It has been proposed that recruitment of vascular mural cells protects tumor endothelium from apoptosis during withdrawal of VEGF. If this were the case, it might be predicted that aSMAimmunopositive vasculature (Morikawa et al. (2002) Am. J. Pathol. 160:985-1000) would not regress during VEGF blockade, or would do so more slowly than endothelial cells alone. However, immunostaining for aSMA demonstrated that this population of cells decreased after one injection of VEGF-Trap and was absent by day 15, in parallel with endothelium.

To examine vascular anatomic changes resulting from this rapid involution of endothelium and perivascular cells in detail, confocal microscopic analysis was performed with pseudo-depth coloring through sections of lectin-perfused tumor one day after the initial injection of VEGF trap. These studies demonstrate that VEGF trap causes not only a rapid decrease in vascularity, but abrupt truncation of vessels, consistent with luminal collapse.

Example 3

Apoptosis in Endothelial and Vascular Mural Cells

PECAM-1, aSMA, and TUNEL Double-staining.

Apoptosis was determined by terminal deoxynucleotidyl transferase-mediated deoxyuridine triphosphate nick-end labeling (TUNEL) staining. Immunofluorescent double-staining for PECAM-1/apoptosis and aSMA/apoptosis was performed on frozen sections using the ApopTag Red In Situ Apoptosis Detection Kit (Intergen Company, Purchase, N.Y.) and either rat anti-mouse PECAM-1 or anti-aSMA monoclonal antibody. A biotinylated secondary antibody was used in combination with fluorescein-labeled avidin to visualize endothelial and vascular mural cells, respectively. Slides were examined and photographed by fluorescence microscopy.

If VEGF-mediated signaling is critical to the survival of both the endothelial and vascular mural cells of mature tumor vessels, apoptosis should be detectable concurrently in both cell populations. Double labeling using the TUNEL assay combined with PECAM-1 and aSMA immunostaining demonstrated apoptosis in both components of xenograft vessels one day after the initial injection of VEGF trap. More widespread apoptosis was observed in endothelial and recruited perivascular cells at day 5 (data not shown). These observations suggest that potent blockade of VEGF rapidly interrupts the endothelial-vascular mural cell signaling which protects both components of tumor vessels from apoptosis. Thus, a certain level of VEGF may be critical to stability even in "mature" tumor vasculature.

Example 4

Alteration in Expression of Angiogenic Factors in Tumors

Expression of VEGF is exquisitely regulated by hypoxia (see, for example, Levy et al. (1995) J. Biol. Chem. 270: 13333-1340), while angiopoietin-2 (Ang-2) is regulated both by VEGF and by hypoxia (Oh et al. (1999) J. Biol. Chem. 274:15732-15739). Concurrent expression of VEGF and Ang-2 may therefore serve as an indication of the physiologic response of tumor cells to hypoxia, which normally promotes angiogenic remodeling and new capillary sprouting (Maisonpierre et al. (1997) Science 277:55-60). In addition, Ang-2 can cause vessel involution when VEGF is deficient (Holash et al. (1999) supra). It was reasoned that tumors regressing solely as a result of vascular involution should exhibit global upregulation of these factors, but decreased expression of VEGFR-2, a marker for growing vasculature. Thus, VEGF, Ang-2, and VEGFR-2 expression was investigated by in situ hybridization.

In situ Hybridization.

Tissue was initially preserved in 4% paraformaldehyde overnight, transferred to 17% sucrose, and embedded in OCT compound and frozen. Tissue sections were then probed with 35S-labeled cRNA with probes hybridizing to human VEGF, Ang-2, or mouse VEGFR-2 as previously described (Holash et al. (1999) Science 284:1994-1998, herein specifically incorporated by reference in its entirety).

Results.

Expression of VEGF and Ang-2 increased markedly between day 0 and day 36. Conversely, expression of VEGFR-2 in tumors decreased over the same period, consistent with the disappearance of endothelial cells expressing this receptor.

Example 5

Regression of Established Lung Metastases During VEGF Trap Administration

Blockade of VEGF has previously been shown to decrease subsequent formation of lung micromretastases in the model used (Rowe et al. (2000) J. Pediatr. Surg. 35:30-33). However, the role of VEGF in maintenance of lung metastases is unknown.

Analysis of Metastases.

Three different levels of hematoxylin and eosin-stained sections through the entire lung of each tumor-bearing animal were examined for metastasis. Cells per metastasis were counted and metastasis diameters measured independently by two observers, and the numbers averaged. Volume was calculated by the standard formula (length)×(width)2× (0.5).

Statistical Analysis.

Comparisons of image analysis measurements, tumor weights and metastasis measurements (cell count, largest diameter, and volume) were performed using Kruskal-Wallis analysis.

Results.

Figure 3:
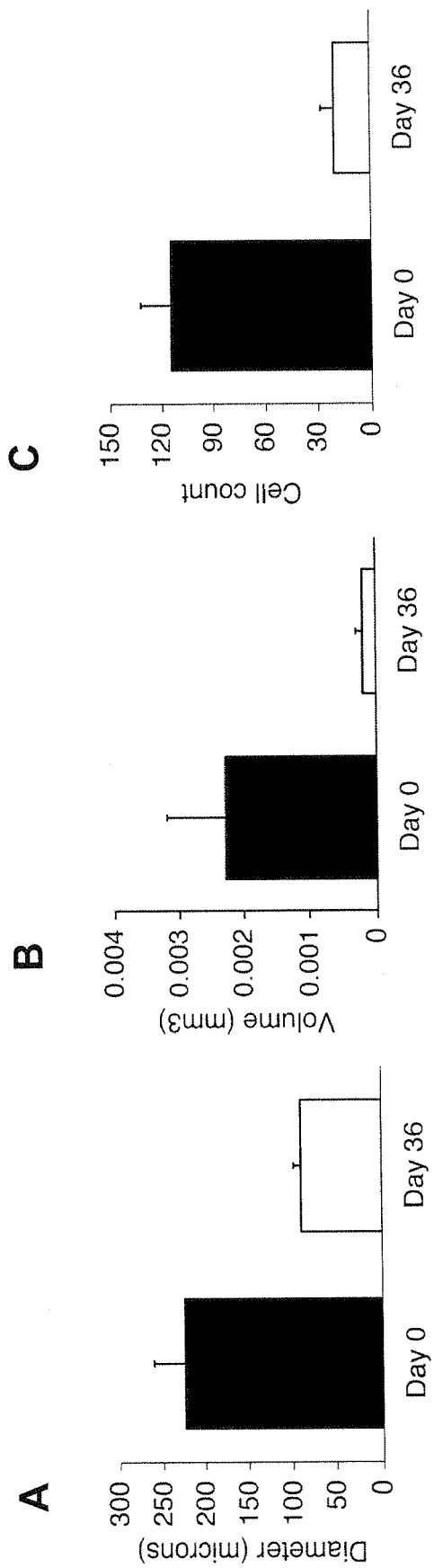
FIG. 3. Effect of VEGF trap on pulmonary metastases. The incidence of pulmonary metastasis and the pattern of adjacent lung microvessels in tumor-bearing animals did not change significantly during VEGF trap administration, but diameter (A), volume (B), and cell count (C) significantly decreased.

The results found that 60% of mice at day 0, and 50% of VEGF trap treated mice at day 36 had lung metastases, and that the number of established metastases had not significantly changed. However, pulmonary tumor deposits were strikingly smaller in the VEGF trap treated lungs in comparison to controls. The size of the pulmonary lesions was quantified at day 0 and 36 by diameter (FIG. 3A), volume (FIG. 3B), and individual cell count (FIG. 3C). There was a significant decrease in the size of the pulmonary metastases by all 3 measurements. Mean diameter of metastases decreased by 80% (225.27±35.4 m vs. 89.2±8.4 m, P=0.0005), mean volume by 78% (0.0023±0.0009 mm3 to 0.00018±0.0001 mm3, P=0.0004), and mean cell count per metastasis by 83% (115.3±16.9 to 20.1±7.2, P=0.0002). TUNEL assay demonstrated apoptosis in lung metastases after one dose of VEGF trap (data not shown), whereas apoptotic cells were rare in day 0 control metastases. Day 0 metastases were adjacent to lung capillaries, rather than surrounding new vessels, a pattern which was not changed in day 36 metastases.

The present invention may be embodied in other specific forms without departing from the spirit or essential attributes thereof.

We claim:

1. A method of regressing or reducing the size of a tumor, comprising administering to a subject in need thereof a therapeutically effective amount of an agent capable of blocking, inhibiting, or ameliorating vascular endothelial growth factor (VEGF)-mediated activity to a subject in need thereof wherein the tumor is regressed or reduced, wherein the agent is a VEGF-specific fusion protein VEGFR1R2-FcΔC1(a).

2. The method of claim 1, wherein the subject is a human subject having one or more tumors.

3. The method of claim 1, wherein administration is subcutaneous, intraperitoneal, or intravenous.

4. A method of regressing or reducing metastases, comprising administering to a subject in need thereof a therapeutically effective amount of an agent capable of blocking, inhibiting, or ameliorating vascular endothelial growth factor (VEGF)-mediated activity to a subject in need thereof wherein metastases are regressed or reduce, and wherein the agent is VEGF-specific fusion protein VEGFR1R2-FcΔC1(a).

5. A method of treating a tumor such that the tumor is reduced in size, comprising administering to a subject in need thereof a therapeutically effective amount of an agent capable of blocking, inhibiting, or ameliorating vascular endothelial growth factor (VEGF)-mediated activity, wherein the tumor is treated, and wherein the agent is VEGF-specific fusion protein VEGFR1R2-FcΔC1(a).

6. A method of inhibiting metastatic cancer, comprising administering to a subject in need thereof a therapeutically effective amount of an agent capable of blocking, inhibiting, or ameliorating vascular endothelial growth factor (VEGF)-mediated activity, wherein the metastatic cancer is inhibited, and wherein the agent is VEGF-specific fusion protein VEGFR1R2-FcΔC1(a).

* * * * *

SEQUENCE LISTING

```
<160> NUMBER OF SEQ ID NOS: 2

<210> SEQ ID NO 1
<211> LENGTH: 1377
<212> TYPE: DNA
<213> ORGANISM: homo sapiens

<400> SEQUENCE: 1
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtggggatt     480
gacttcaact gggaataccc ttcttcgaag catcagcata agaaacttgt aaaccgagac     540
ctaaaaaccc agtctgggag tgagatgaag aaattttttga gcaccttaac tatagatggt     600
gtaacccgga gtgaccaagg attgtacacc tgtgcagcat ccagtgggct gatgaccaag     660
aagaacagca catttgtcag ggtccatgaa aaggacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta caacagcacg taccgtgtgg tcagcgtcct caccgtcctg     960
caccaggact ggctgaatgg caaggagtac aagtgcaagg tctccaacaa agccctccca    1020
gcccccatcg agaaaaccat ctccaaagcc aaagggcagc cccgagaacc acaggtgtac    1080
accctgcccc catcccggga tgagctgacc aagaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctacagcaag    1260
ctcaccgtgg acaagagcag gtggcagcag gggaacgtct tctcatgctc cgtgatgcat    1320
gaggctctgc acaaccacta cacgcagaag agcctctccc tgtctccggg taaatga      1377
```

-continued

<210> SEQ ID NO 2
<211> LENGTH: 458
<212> TYPE: PRT
<213> ORGANISM: homo sapiens

<400> SEQUENCE: 2

```
Met Val Ser Tyr Trp Asp Thr Gly Val Leu Leu Cys Ala Leu Leu Ser
 1               5                  10                  15

Cys Leu Leu Thr Gly Ser Ser Ser Gly Ser Asp Thr Gly Arg Pro
             20                  25                  30

Phe Val Glu Met Tyr Ser Glu Ile Pro Glu Ile Ile His Met Thr Glu
             35                  40                  45

Gly Arg Glu Leu Val Ile Pro Cys Arg Val Thr Ser Pro Asn Ile Thr
 50                  55                  60

Val Thr Leu Lys Lys Phe Pro Leu Asp Thr Leu Ile Pro Asp Gly Lys
 65                  70                  75                  80

Arg Ile Ile Trp Asp Ser Arg Lys Gly Phe Ile Ile Ser Asn Ala Thr
                 85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
            115                 120                 125

Asp Val Val Leu Ser Pro Ser His Gly Ile Glu Leu Ser Val Gly Glu
        130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380
```

-continued

```
Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```